(12) United States Patent
Chou

(10) Patent No.: US 9,968,487 B2
(45) Date of Patent: May 15, 2018

(54) GLASSES STRUCTURE

(71) Applicant: HSIEN CHANG OPTICAL INDUSTRIAL CO., LTD., Tainan (TW)

(72) Inventor: Wen-Hsiung Chou, Tainan (TW)

(73) Assignee: Hsien Chang Optical Industrial Co., Ltd., Tainan (TW)

( * ) Notice: Subject to any disclaimer, the term of this patent is extended or adjusted under 35 U.S.C. 154(b) by 147 days.

(21) Appl. No.: 15/074,001

(22) Filed: Mar. 18, 2016

(65) Prior Publication Data
US 2017/0266049 A1    Sep. 21, 2017

(51) Int. Cl.
G02C 9/04      (2006.01)
A61F 9/02      (2006.01)
G02C 9/00      (2006.01)
G02C 1/00      (2006.01)

(52) U.S. Cl.
CPC .............. *A61F 9/026* (2013.01); *G02C 9/00* (2013.01); *G02C 9/04* (2013.01); *G02C 1/10* (2013.01)

(58) Field of Classification Search
CPC .. A61F 9/026; G02C 1/06; G02C 1/10; G02C 9/04; G02C 9/00
USPC ................... 351/86, 47, 154, 41; 2/440–441
See application file for complete search history.

(56) References Cited

U.S. PATENT DOCUMENTS

| | | | | |
|---|---|---|---|---|
| 6,641,263 B2* | 11/2003 | Olney | ..................... | A61F 9/026 2/436 |
| 8,366,266 B2* | 2/2013 | Pulito | ..................... | A61F 9/026 351/62 |
| 2009/0079931 A1* | 3/2009 | Yang | ........................ | G02C 9/00 351/60 |

* cited by examiner

*Primary Examiner* — Ricky Mack
*Assistant Examiner* — Kristina Deherrera
(74) *Attorney, Agent, or Firm* — Rosenberg, Klein & Lee

(57) ABSTRACT

A glasses structure comprises a main body and a sub-frame assembled at the rear of a lens of the main body. The inner surface of a frame body of the sub-frame is attached with a pad, which pad is formed with an upper contact portion and a central contact portion corresponding to the upper edge and the central shape of the frame body. Two nose pieces are formed at the both sides of the central contact portion of the pad, and the upper contact portion of the pad are respectively contacted with the user's nose and forehead to avoid pain when the user wears the glasses. Furthermore, the colored and patterned frame body of the sub-frame is shown from the transparent lens of the main body, whereby the glasses with suitable color and pattern being chosen to dress with the user's clothes and style, increasing the user's fashion and beauty.

5 Claims, 4 Drawing Sheets

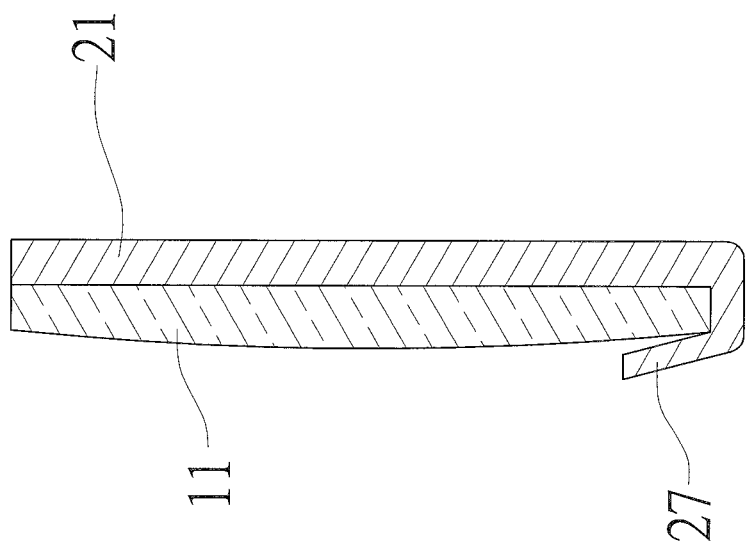

GLASSES STRUCTURE

BACKGROUND OF THE INVENTION

Field of the Invention

The present invention relates to a glasses structure. More particularly, the disclosure relates to a glasses structure for increasing the wearing comfort and enhancing the beauty of glasses.

Description of Related Art

At the general construction site, the worker usually wears the safety glasses. The existing safety glasses comprises lens which is made of hard plastic material such as polycarbonate (PC) etc. and two wearing portions assembled at the both sides of the lens respectively. The two wearing portions are worn on the worker's ears, and the nose piece formed at the center of the lens is supported on the worker's nose, so the lens is covered the worker's eyes to protect the worker's eyes from damage caused by the gravel, scrap iron, spark, or corrosion.

However, in order to effectively prevent the gravel, scrap iron, spark, or corrosion from injuring the worker's eye from the opening between the worker's face and safety glasses, the existing safety glasses is tightly contacted with the worker's face. Because the material of the lens of the safety glasses is hard, it easily causes pain when the worker wears the safety glasses. In addition, as the people have the higher and higher demand for the goods quality, the safety glasses not only has the function for protection eyes from damage caused by the foreign article, but also has comfort and beauty, as well as the glasses could be matched with the user's style. Accordingly, the safety glasses which only have the function for protection eyes from damage caused by the foreign article do not accord with the market demand.

SUMMARY OF THE INVENTION

Therefore, the object of the present invention is related to a glasses structure for increasing the wearing comfort and enhancing the beauty of glasses.

For the above object, a glasses structure comprises a main body and a sub-frame.

The main body comprises a lens, a first reverse V-shaped notch, and two wearing portions. The first reverse V-shaped notch is formed at the central lower edge of the lens, and the two wearing portions are assembled at the both sides of the lens respectively.

The sub-frame is assembled at the rear of the lens of the main body and comprises a frame body, two windows, a pad, two nose pieces, a first clip, and a two and a third clip. The shape of the frame body is corresponded to the shape of the lens of the main body, and the central lower edge of the frame body is formed with a second reverse V-shaped notch. The two windows are formed at the both sides of the center of the frame body respectively. The pad is attached at the inner surface of the frame body and comprises an upper contact portion and a central contact portion, wherein the shape of the upper contact portion is corresponded to an upper edge of the frame body and the shape of the central contact portion is corresponded to the shape of the center of the frame body. The two nose pieces are formed at the central contact portion and corresponded to the both sides of the notch of the frame body respectively. The first clip is formed at the outer central upper edge of the frame body for holding on the central upper edge of the lens of the main body. The second and the third clip are respectively formed at the outer lower edge of both sides of the frame body for holding on the lower edge of the lens of the main body.

According to an embodiment of the present invention, two nose pads are respectively formed at the inner surface of the lens of the main body and close to the both sides of the notch of the frame body, and the both sides of the notch of the frame body are formed with a recess respectively, whereby embedding the nose pads into the recesses.

According to an embodiment of the present invention, the lens of the main body is transparent, and the frame body of the sub-frame is colored, patterned, or combined.

According to an embodiment of the present invention, the upper contact portion and the central contact portion of the pad are integrally formed.

Accordingly, the nose pieces and the upper contact portion of the pad are respectively contacted with the user's nose and forehead to avoid the pain when user wears glasses. Furthermore, the colored and patterned frame body of the sub-frame is shown from the transparent lens of the main body, whereby the glasses with suitable color and pattern being chosen to dress with the user's clothes and style, increasing the user's fashion and beauty.

BRIEF DESCRIPTION OF THE DRAWINGS

FIG. 4 is another partial-sectional view of FIG. 1.

DETAILED DESCRIPTION OF THE PREFERRED EMBODIMENT

Figure 1:
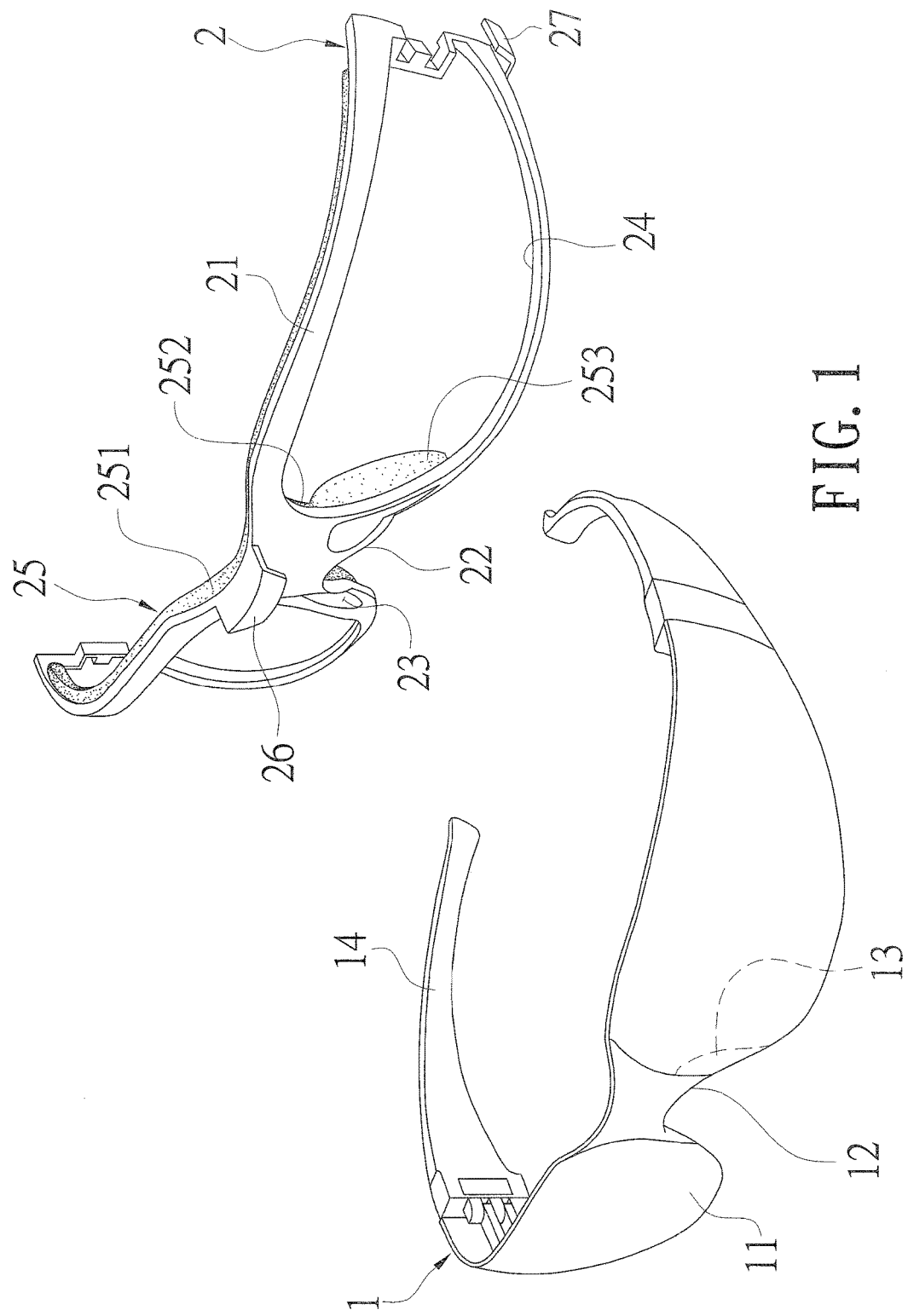
FIG. 1 is an exploded view of a glasses structure according to an embodiment of the present invention.
Figure 2:
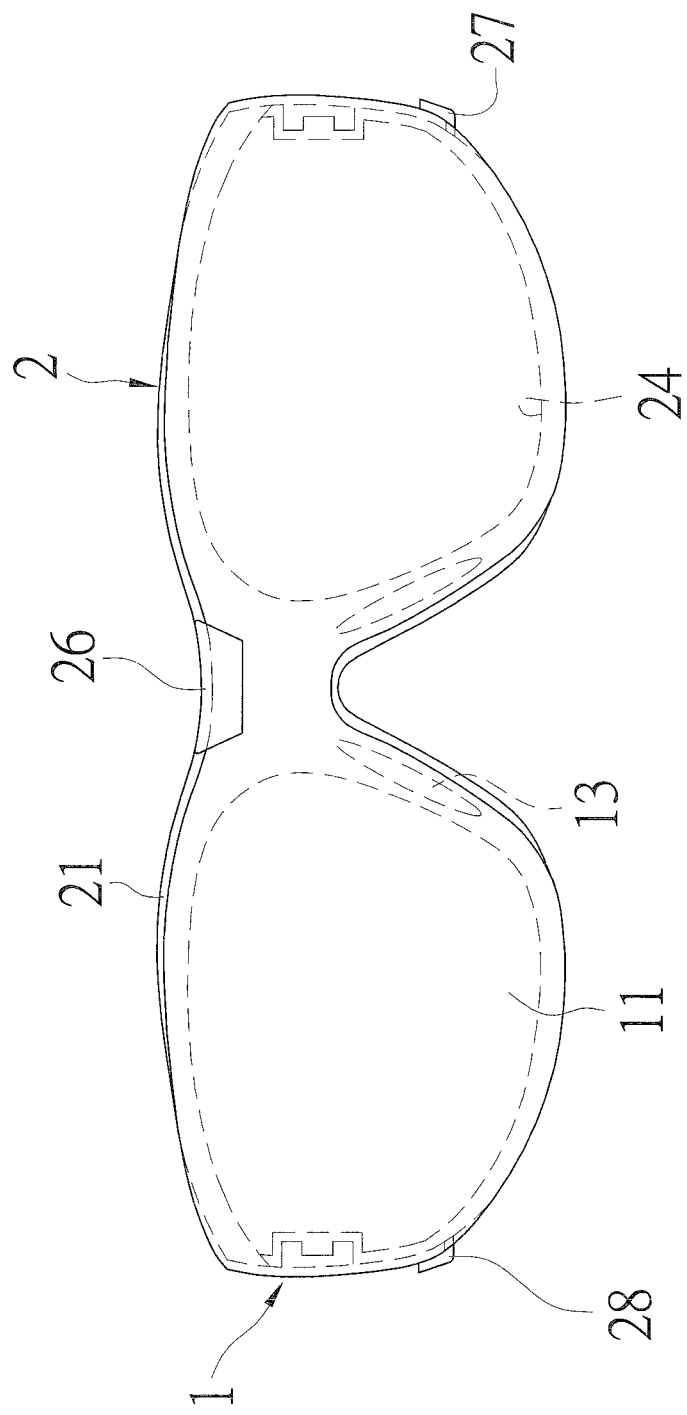
FIG. 2 is a front view of FIG. 1.
Figure 3:
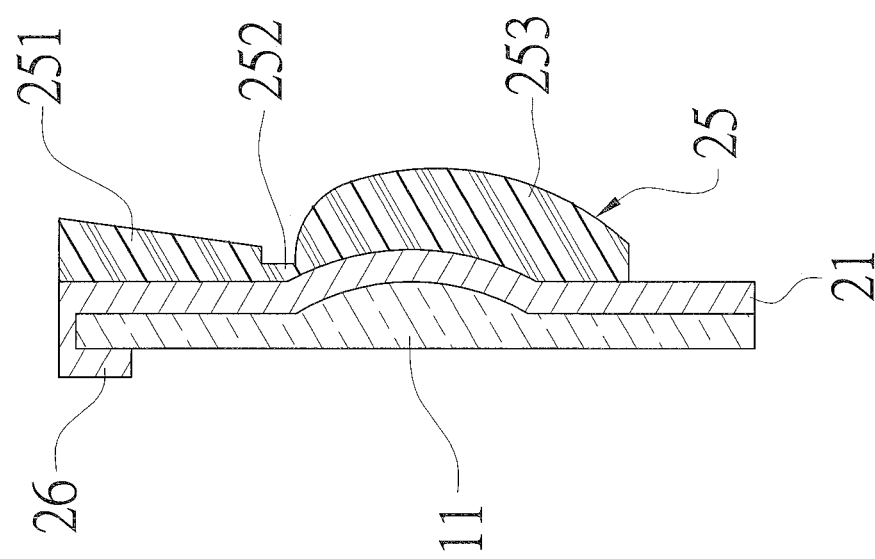
FIG. 3 is a partial-sectional view of FIG. 1.

Please refer to FIG. 1 to FIG. 4, which are an exploded view, a front view, and two different partial-sectional views of a glasses structure according to an embodiment of the present invention, respectively. The glasses structure comprises a main body 1 and a sub-frame 2.

The main body 1 comprises a lens 11, a first reverse V-shaped notch 12, two nose pads 13, and two wearing portions 14. The lens 11 is a transparent lens which is integrally made of hard plastic material such as polycarbonate (PC) etc. The first reverse V-shaped notch 12 is formed at the central lower edge of the lens 11. The two nose pads 13 are respectively formed at the inner surface of the lens 11 and close to the both sides of the notch 12. The two wearing portions 14 are assembled at the both sides of the lens 11 respectively.

The sub-frame 2 is assembled at the rear of the lens 11 of the main body 1 and comprises a frame body 21, a second reverse V-shaped notch 22, two recesses 23, two windows 24, a pad 25, a first clip 26, a second clip 27, and a third clip 28. The frame body 21 is plastic and is colored, patterned, or combined, and the shape of the frame body 21 is corresponded to the shape of the lens 11 of the main body 1. The second reverse V-shaped notch 22 is formed at the central lower edge of the frame body 21, and the two recesses 23 are respectively formed at the both sides of the notch 22 and at the outer surface of the frame body 21 for embedding the nose pads 13 into the recesses 23, which the nose pads 13 are formed at the inner surface of the lens 11 and close to the both sides of the notch 12 of the main body 1. The two windows 24 are formed at the both sides of the center of the frame body 21 respectively. The pad 25 is attached at the inner surface of the frame body 21 and comprises an upper contact portion 251 and a central contact portion 252. In detail, the shape of the upper contact portion 251 is corresponded to an upper edge of the frame body 21, and the shape of the central contact portion 252 is corresponded to the shape of the center of the frame body 21. The central contact portion 252 is formed with two nose pieces 253, which nose pieces 253 are respectively corresponded to the both sides of the notch 22 of the frame body 21. The first clip 26 is formed at the outer central upper edge of the frame body 21 for holding on the central upper edge of the lens 11 of the main body 1, moreover, the second clip 27 and the third clip 28 are respectively formed at the outer lower edge of the both sides of the frame body 21 for holding on the lower edge of the lens 11 of the main body 1.

Accordingly, when the glasses structure of the present invention is assembled, the sub-frame 2 is assembled at the rear of the lens 11 of the main body 1, and the second clip 27 and the third clip 28 which are formed at the outer lower edge of the both sides of the frame body 21 of the sub-frame 2 are hold on the lower edge of the both sides of the lens 11 of the main body 1. Then, the two nose pads 13 which are at the notch 12 of the inner surface of the lens 11 of the main body 1 are embedded into the recesses 23 which are formed at the frame body 21 of the sub-frame 2 and close to the both sides of the notch 22. Next, the upper edge of the frame body 21 of the sub-frame 2 is slightly pulled for the first clip 26, which first clip 26 is at the upper edge of the frame body 21, being held on the central upper edge of the lens 11 of the main body 1. Therefore, the second clip 27 and the third clip 28, which are at the lower edge of the both side of the frame body 21 of the sub-frame 2, and the first clip 26, which is at the upper edge of the frame body 21, are formed a three-point positioning in order to stably assemble the sub-frame 2 with the lens 11 of the main body 1. Furthermore, the two nose pads 13, which are at the center of the lens 11 of the main body 1, are embedded into the two recesses 23, which are at the center of the frame body 21 of the sub-frame 2, enhancing the firmness between the main body 1 and the sub-frame 2.

The user can wear the glasses structure of the present invention during construction. When wearing, the two wearing portions 14 of the main body 1 are worn on the user's ear, and the two nose pieces 253, which is formed at the inner surface of the pad 25 of the sub-frame 2, are supported on the both sides of the user's nose, furthermore, the upper contact portion 251 of the pad 25 is contacted with the user's forehead. Therefore, the lens 11 of the main body 1 covers the user's eyes when the glasses structure of the present invention is worn. In the other words, during construction, the user can watch clearly the work items and machine through the windows 24 of the frame body 21 via the transparent lens 11 for keeping the construction safety, and by the covering of the lens 11 of the main body 1, the user's eyes are avoided injury from the splash of gravel, scrap iron, spark, or corrosion. The nose pieces 253 and the upper contact portion 251 are contacted with the user's nose and forehead to be the supporting point when the glasses are worn, so it avoids the pain that is caused by the directly contact of the lens 11 of the hard main body 1 with the user's nose and forehead, increasing the comfort of the glasses structure of the present invention in use. Besides, the frame body 21 of the sub-frame 2 is colored and patterned, the color and pattern of the frame body 21 are shown from the transparent lens 11 of the main body 1 to enhance the beauty of the glasses structure of the present invention, whereby the glasses with suitable color and pattern being chosen to dress with the user's clothes and style, increasing the user's fashion and beauty.

However, the foregoing embodiments and drawings does not limits the product structures or uses of the present invention, it will be is obvious to those skilled in the art that various modifications may be made without departing from the spirit and the scope of the present invention.

According to the above description and embodiments, the glasses structure of the present invention has the advantages as following:

1. In the glasses structure of the present inventions,
2. In the glasses structure of the present invention, the frame body of the sub-frame is colored or patterned, the color and pattern of the frame body are shown from the transparent lens of the main body, whereby the glasses with suitable color and pattern being chosen to dress with the user's clothes and style, increasing the user's fashion and beauty.
3. In the glasses structure of the present invention, the first clip, the second clip and the third clip, which are at the upper edge and the lower edge of the both sides of the frame body of the sub-frame, are formed a three-point positioning in order to stably assemble the sub-frame with the main body. Furthermore, the nose pads, which are at the center of the lens of the main body, are embedded into the recesses, which are at the center of the frame body of the sub-frame, enhancing the firmness between the main body and the sub-frame.
4. The glasses structure of the present invention could be assembled with the existing glasses without changing the existing glasses structure, improving the convenience of the glasses structure of the present invention.

What is claimed is:
1. A glasses structure, comprising:
   a main body including:
      a lens-holding portion including at least one lens, a central lower edge of the lens-holding portion having a first reverse V-shaped notch formed therein,
      two nose pads formed at an inner surface of the lens-holding portion, each nose pad formed proximate to a respective side of the first reverse V-shaped notch, and
      two wearing portions respectively assembled at each side of the lens-holding portion; and
   a sub-frame assembled at a rear of the lens of the main body, the sub-frame including:
      a frame body corresponding in shape to the lens-holding portion of the main body, a central lower edge of the frame body having a second reverse V-shaped notch formed therein, two windows being respectively formed within each side of a center of the frame body, two recesses being formed in the frame body respectively proximate to each side of the notch, each of the recesses being configured to receive a respective one of the nose pads of the main body,
      a pad attached at an inner surface of the frame body, the pad including an upper contact portion and a central contact portion, the upper contact portion corresponding in shape to an upper portion of the frame body, the central contact portion corresponding in shape to the center of the frame body,
      two nose pieces formed at the central contact portion and respectively corresponding to each side of the second reverse V-shaped notch of the frame body, a first clip formed at an outer central upper edge of the frame body, the first clip extending over a central upper edge and front surface of the lens-holding portion of the main body, and a second clip and a third clip respectively formed at an outer lower edge of each side of the frame body, the second and third clips each extending over a lower edge and the front surface of the lens-holding portion of the main body to thereby capture the main body in cooperation with the first clip.

2. The glasses structure according to claim 1, wherein the lens of the lens-holding portion of the main body is transparent, and the frame body of the sub-frame is colored and/or patterned.

3. The glasses structure according to claim 1, wherein the upper contact portion and the central contact portion of the pad are integrally formed.

4. A sub-frame adapted to be fitted to a standard pair of glasses having a continuous lens periphery, the sub-frame comprising: a frame body corresponding in shape to a lens-holding portion of a standard pair of glasses having a continuous lens periphery, a central lower edge of the frame body having a reverse V-shaped notch formed therein, two windows being respectively formed within each side of a center of the frame body, two recesses being formed in the front of the frame body respectively proximate to each side of the notch, each of the recesses being configured to receive a respective nose pad of the standard pair of glasses; a first clip formed at an outer central upper edge of the frame body, the first clip being configured to extend over a central upper edge and front surface of the lens-holding portion of the standard pair of glasses; and a second clip and a third clip respectively formed at an outer lower edge of each side of the frame body, the second and third clip each being configured to extend over a lower edge and the front surface of the lens-holding portion of the standard pair of glasses to thereby capture the standard pair of glasses in cooperation with the first clip.

5. The sub-frame of claim 4, further comprising:

a pad attached at an inner surface of the frame body, the pad including an upper contact portion and a central contact portion, the upper contact portion corresponding in shape to an upper portion of the frame body, the central contact portion corresponding in shape to the center of the frame body; and two nose pieces formed at the central contact portion and respectively corresponding to each side of the reverse V-shaped notch of the frame body.

* * * * *